(12) United States Patent
Brooks

(10) Patent No.: US 11,006,683 B1
(45) Date of Patent: May 18, 2021

(54) SANITARY WIPE GLOVE

(71) Applicant: La Veda Brooks, New Milford, CT (US)

(72) Inventor: La Veda Brooks, New Milford, CT (US)

(*) Notice: Subject to any disclaimer, the term of this patent is extended or adjusted under 35 U.S.C. 154(b) by 0 days.

(21) Appl. No.: 16/525,677

(22) Filed: Jul. 30, 2019

(51) Int. Cl.
A41D 19/00 (2006.01)
A61B 42/10 (2016.01)
A61M 35/00 (2006.01)
A61F 13/40 (2006.01)

(52) U.S. Cl.
CPC ..... *A41D 19/0075* (2013.01); *A41D 19/0006* (2013.01); *A61B 42/10* (2016.02); *A61M 35/006* (2013.01); *A61M 35/10* (2019.05); *A41D 2300/22* (2013.01)

(58) Field of Classification Search
CPC . A41D 19/006; A41D 19/0075; A61M 35/10; A61M 35/006
USPC .......................................................... 2/161.7
See application file for complete search history.

(56) References Cited

U.S. PATENT DOCUMENTS

| | | | |
|---|---|---|---|
| 4,902,283 A * | 2/1990 | Rojko | A41D 19/0068 15/227 |
| 6,146,365 A | 11/2000 | Nguyen | |
| D468,870 S | 1/2003 | Bufford | |
| 6,511,111 B2 | 1/2003 | Dooley | |
| 6,516,469 B1 * | 2/2003 | Schaetzel | A41D 19/0075 119/850 |
| 7,681,250 B2 * | 3/2010 | Friedstrom | A47K 7/02 2/158 |
| 7,725,979 B1 | 6/2010 | Held | |
| 7,761,931 B2 | 7/2010 | Schrodl | |
| D758,020 S | 5/2016 | Santini | |
| 2005/0125877 A1 * | 6/2005 | Benjamin | A41D 19/01 2/158 |
| 2006/0097122 A1 * | 5/2006 | Collins | A47K 5/08 248/317 |
| 2007/0048062 A1 * | 3/2007 | Brunner | A47L 21/04 401/7 |
| 2009/0064392 A1 * | 3/2009 | Rachuba, IV | A41D 19/01 2/158 |
| 2012/0216329 A1 * | 8/2012 | Dennis | B65D 33/002 2/158 |
| 2014/0096795 A1 * | 4/2014 | Farber | A47L 13/19 134/6 |
| 2014/0373250 A1 * | 12/2014 | Neault | A41D 19/015 2/158 |
| 2016/0272395 A1 * | 9/2016 | Weldon | A45D 40/26 |

* cited by examiner

Primary Examiner — Gloria M Hale

(57) ABSTRACT

The sanitary wipe glove is a pre-moistened wipe. The sanitary wipe glove is configured for use with a patient. The sanitary wipe glove is worn on the patient. The patient uses the sanitary wipe glove for personal cleansing and hygiene. The sanitary wipe glove comprises a glove, an elastic band, and a cleansing agent. The elastic band attaches to the glove. The cleansing agent is a liquid phase solution that is absorbed into the glove. The glove is worn on the hand of the patient.

6 Claims, 3 Drawing Sheets

SANITARY WIPE GLOVE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including toilet preparations, more specifically, a toilet preparation characterized by a special physical form. (A61K8/02)

SUMMARY OF INVENTION

The sanitary wipe glove is a pre-moistened wipe. The sanitary wipe glove is adapted for use with a patient. The sanitary wipe glove is worn on the patient. The patient uses the sanitary wipe glove for personal cleansing and hygiene. The sanitary wipe glove comprises a glove, an elastic band, and a cleansing agent. The elastic band attaches to the glove. The cleansing agent is a liquid phase solution that is absorbed into the glove. The glove is worn on the hand of the patient.

These together with additional objects, features and advantages of the sanitary wipe glove will be readily apparent to those of ordinary skill in the art upon reading the following detailed description of the presently preferred, but nonetheless illustrative, embodiments when taken in conjunction with the accompanying drawings.

In this respect, before explaining the current embodiments of the sanitary wipe glove in detail, it is to be understood that the sanitary wipe glove is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the sanitary wipe glove.

It is therefore important that the claims be regarded as including such equivalent construction insofar as they do not depart from the spirit and scope of the sanitary wipe glove. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
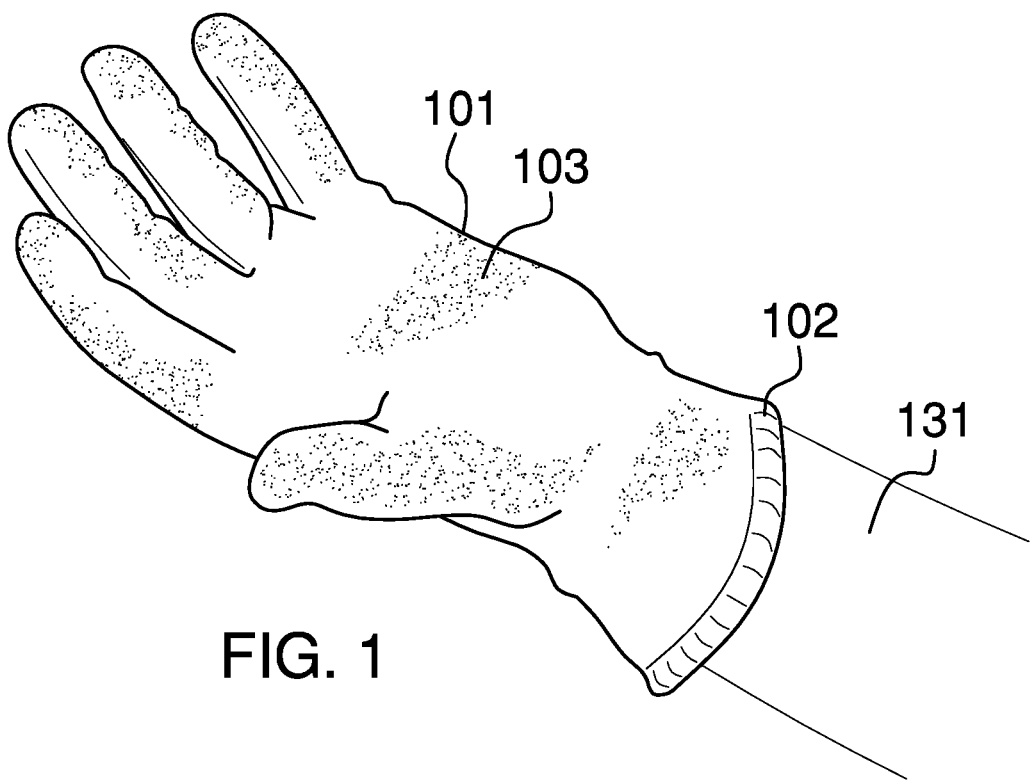
FIG. 1 is a perspective view of an embodiment of the disclosure.
Figure 2:
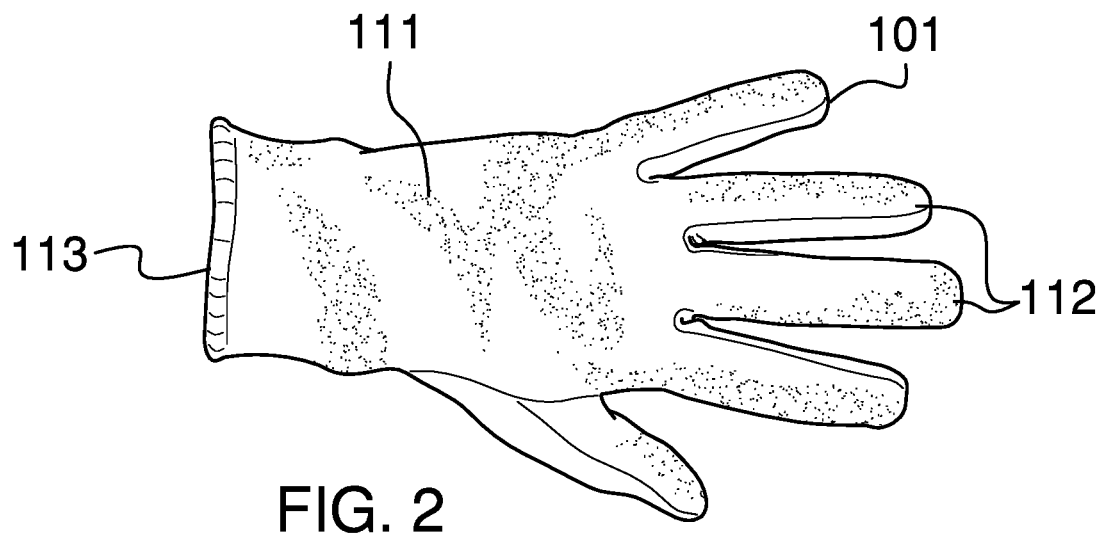
FIG. 2 is a rear view of an embodiment of the disclosure.
Figure 3:
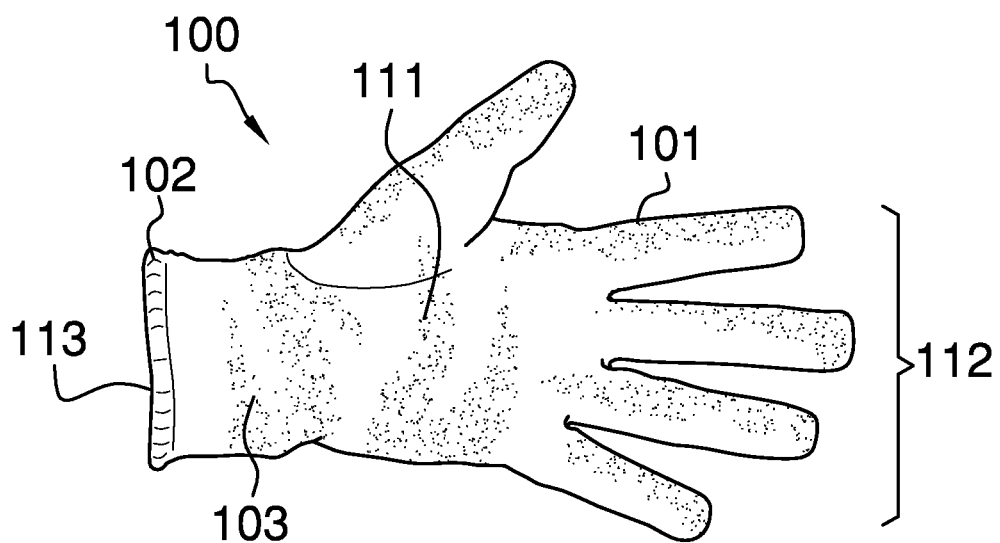
FIG. 3 is a front view of an embodiment of the disclosure.
Figure 4:
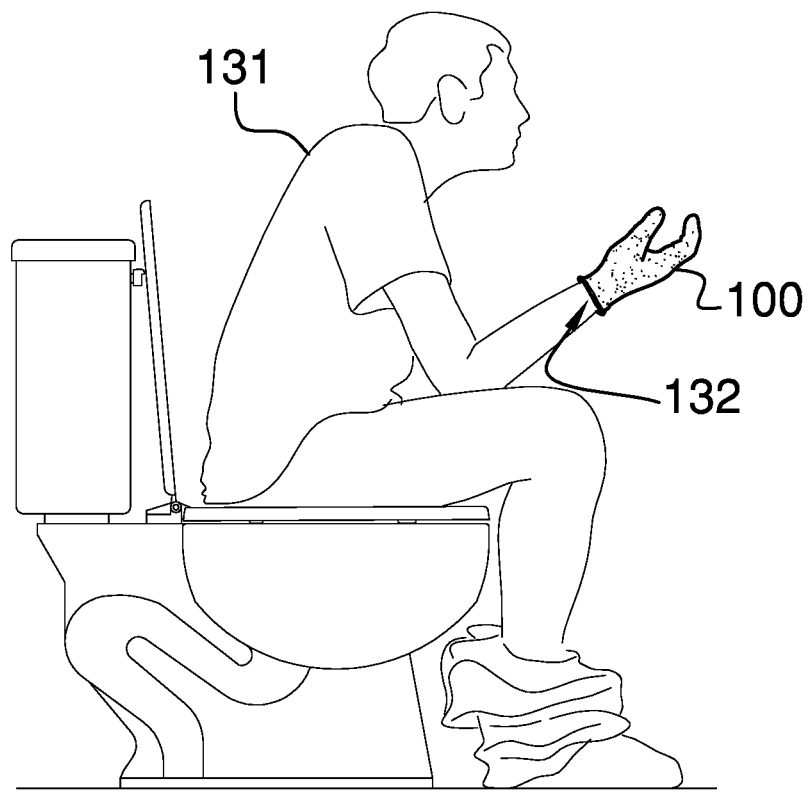
FIG. 4 is an in-use view of an embodiment of the disclosure.
Figure 5:
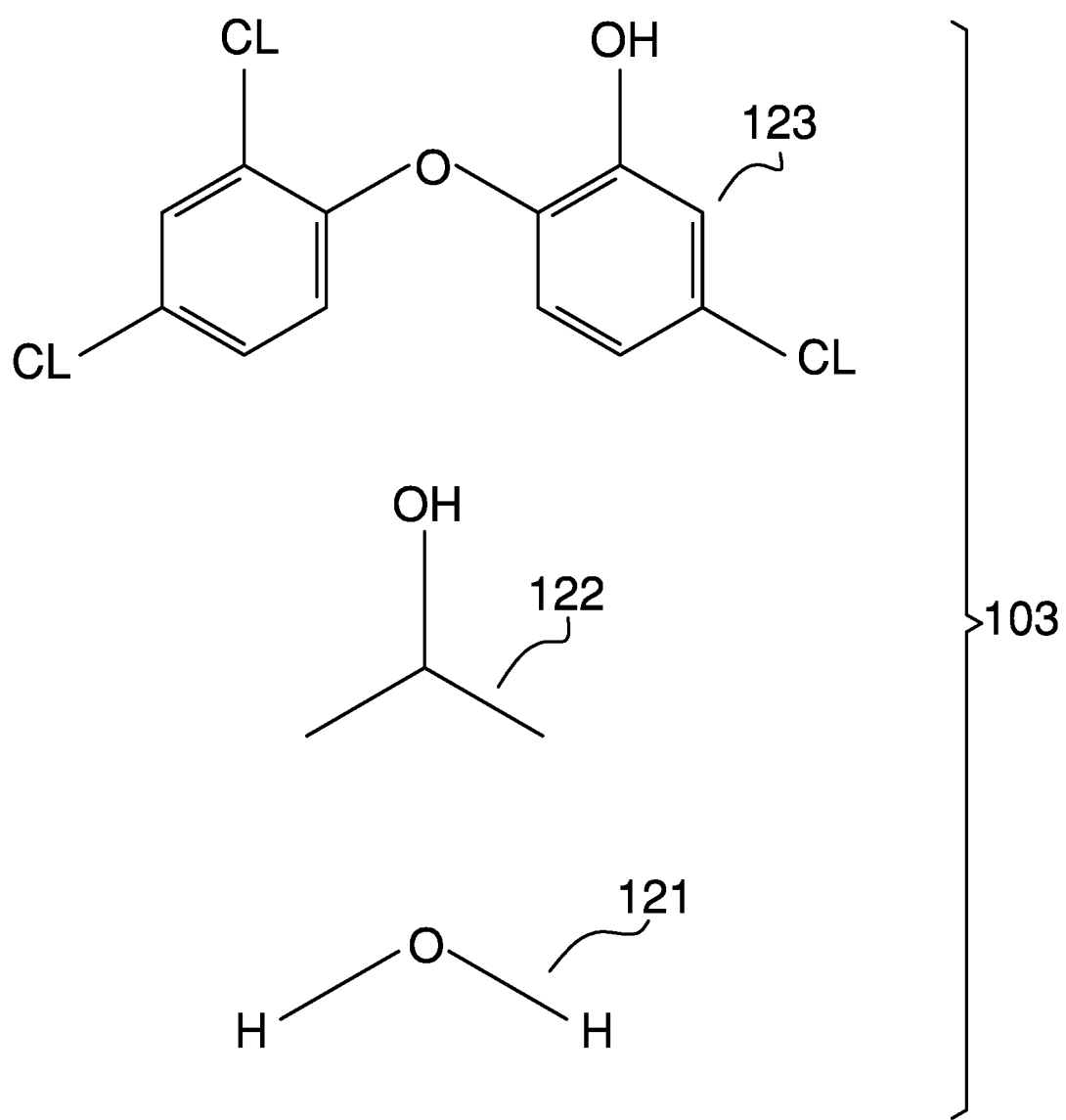
FIG. 5 is a detail view of an embodiment of the disclosure.

Detailed reference will now be made to one or more potential embodiments of the disclosure, which are illustrated in FIGS. 1 through 5.

The sanitary wipe glove 100 (hereinafter invention) is a pre-moistened wipe. The invention 100 is configured for use with a patient 131. The invention 100 is worn on the patient 131. The patient 131 uses the invention 100 for personal cleansing and hygiene. The invention 100 comprises a glove 101, an elastic band 102, and a cleansing agent 103. The elastic band 102 attaches to the glove 101. The cleansing agent 103 is a liquid phase solution that is absorbed into the glove 101. The glove 101 is worn on the hand 132 of the patient 131. The patient 131 is defined elsewhere in this disclosure. The hand is defined elsewhere in this disclosure.

The glove 101 is an apparel item. The glove 101 is worn on the hand 132 of the patient 131. The glove 101 is formed from an absorbent material. In the first potential embodiment of the disclosure, the glove 101 is formed from cotton. The glove 101 is saturated in the cleansing agent 103 such that the glove 101 can be stored in the manner of a pre-moistened wipe. Methods to store one or more pre-moistened wipes in a saturated state are well-known and documented in the chemical arts. The gloved 101 hand 132 is wiped across the body of the patient 131 such that the glove 101 will clean the body of the patient 131 in the manner of a pre-moistened wipe. The pre-moistened wipe is defined elsewhere in this disclosure. The glove 101 comprises a trank 111, a plurality of finger stalls 112, and an opening 113.

The trank 111 is the portion of the glove 101 that encloses 11 the palm of the hand 132 of the patient 131. The trank 111 is formed from an absorbent material. The trank 111 is saturated by the cleansing agent 103 during storage of the glove 101. The trank 111 is defined elsewhere in this disclosure.

Each of the plurality of finger stalls 112 is a sleeve that attaches to the trank 111 of the glove 101. Each of the plurality of finger stalls 112 is sized and positioned to receive a finger from the hand 132 of the patient 131. Each of the plurality of finger stalls 112 is a tubular structure that encloses a finger of the hand 132 of the patient 131. The plurality of finger stalls 112 is formed from an absorbent material. Each of the plurality of finger stalls 112 is saturated by the cleansing agent 103 during storage of the glove 101.

The trank 111 and the plurality of finger stalls 112 are rubbed against the body of the patient 131 such that the cleansing agent 103 is applied to the patient 131 during the cleaning process.

The opening 113 is an aperture formed within the trank 111 of the glove 101. The position of the opening 113 in the trank 111 is distal from the plurality of finger stalls 112. The opening 113 receives the hand 132 of the patient 131 when the glove 101 is donned.

The elastic band 102 is an elastic loop that is formed around the opening 113 in the trank 111 of the glove 101 that receives the hand 132 of the patient 131. The elastic band 102 secures the glove 101 to the hand 132 of the patient 131 during the use of the invention 100.

The elastic band 102 acts as a spring. Specifically, when a hand 132 of the patient 131 inserts through the elastic band 102, the pressing of the hand 132 of the patient 131 against the elastic band 102 applies a force that displaces the elastic band 102 in a direction that is perpendicular to the center axis of the elastic band 102. The elasticity of the elastic band 102 creates a force that opposes the displacement created by the insertion of the hand 132 of the patient 131 into the elastic band 102. This opposing force is in a direction that returns the elastic band 102 to its relaxed shape. Because the hand 132 of the patient 131 prevents the elastic band 102 from returning completely to its relaxed shape, the elastic band 102 applies a force against the hand 132 of the patient 131 that secures the elastic band 102 in position thereby holding the glove 101 in position.

The cleansing agent 103 is a chemical solution. The cleansing agent 103 is an antimicrobial compound that is applied to the body of the patient 131 by the glove 101. The glove 101 and the cleansing agent 103 are rubbed against the body of the patient 131 in order to clean the patient 131. The cleansing agent 103 is a liquid phase solution comprising water (CAS 7732-18-5) 121, an alcohol 122, and an antimicrobial agent 123.

The water (CAS 7732-18-5) 121 is the solvent used in the solution that forms the cleansing agent 103.

The alcohol 122 is an organic chemical compound that is formed with a hydroxyl group. The alcohol 122 dissolves in the water (CAS 7732-18-5) 121. The alcohol 122 acts as a disinfecting agent when applied to the body of the patient 131. The alcohol 122 acts as a preservative that inhibits the growth of bacteria and fungi while the invention 100 is in storage. The use of an alcohol 122 for this purpose is well known and documented in the chemical and medical arts.

The antimicrobial agent 123 is an organic chemical compound. The antimicrobial agent 123 dissolves in the water (CAS 7732-18-5) 121 and alcohol 122 solution. The antimicrobial agent 123 kills and inhibits the growth microorganisms found on the skin of the patient 131. The use of an antimicrobial agent 123 for this purpose is well known and documented in the chemical and medical arts.

In the first potential embodiment of the disclosure, the antimicrobial agent 123 is selected from the group consisting of 5-chloro-2-(2,4-dichlorophenoxy)-phenol (CAS 3380-34-5) and N-(4-chlorophenyl)-N'-(3,4-dichlorophenyl)-urea (CAS 101-20-2). The alcohol 122 is 2-proponal (CAS 67-63-0).

The 2-proponal (CAS 67-63-0) is an alcohol 122 commonly referred to as isopropyl alcohol 122. The 2-proponal (CAS 67-63-0) is defined elsewhere in this disclosure.

The 5-chloro-2-(2,4-dichlorophenoxy)-phenol (CAS 3380-34-5) is an antimicrobial and an antifungal compound. The 5-chloro-2-(2,4-dichlorophenoxy)-phenol (CAS 3380-34-5) is defined elsewhere in this disclosure.

The N-(4-chlorophenyl)-N'-(3,4-dichlorophenyl)-urea (CAS 101-20-2) is an antimicrobial compound. The N-(4-chlorophenyl)-N'-(3,4-dichlorophenyl)-urea (CAS 101-20-2) is defined elsewhere in this disclosure.

The following definitions were used in this disclosure:

2-proponal: As used in this disclosure, 2-proponal (CAS 67-63-0) is a chemical substance with the chemical formula C3H7OH. 2-proponal is also known as isopropyl alcohol.

2-pyrrolidinone with iodine: As used in this disclosure, 2-pyrrolidinone with iodine (CAS 25655-41-8) is a topical disinfectant chemical substance commonly referred to as povidone-iodine.

5-chloro-2-(2,4-dichlorophenoxy)-phenol: As used in this disclosure, 5-chloro-2-(2,4-dichlorophenoxy)-phenol (CAS 3380-34-5) is an antifungal and antimicrobial agent that is commonly used in consumer products. 5-chloro-2-(2,4-dichlorophenoxy)-phenol is commonly referred to as triclosan.

Absorbent: As used in this disclosure, absorbent is an adjective that refers to a material that is able to soak up a liquid such as water.

Alcohol: As used in this disclosure, an alcohol refers to an organic chemical structure that comprises a hydroxyl functional group.

Cotton: As used in this disclosure, cotton is a fibrous material derived from the cotton plant. Cotton has a cellulose structure and is commonly used in the formation of yarns used in textile products.

Don: As used in this disclosure, to don means to enclose a person or object within a structure. For example, a person dons a helmet.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elastic Band: As used in this disclosure, an elastic band is a loop of textile that is formed using elastic material that can stretch. Alternatively, the elastic band can be a sheeting that is formed from latex, spandex, or an elastic plastic film that can be stretched.

Elimination: As used in this disclosure, an elimination refers to a solid phase discharge from a biological entity.

Finger Stall: As used in this disclosure, a finger stall refers to: 1) the roughly cylindrical structure associated with a glove into which a finger may be inserted; or, 2) a roughly cylindrical cover, commonly referred to as a finger cot, that is placed directly over a finger to cover the finger. A finger stall is also referred to as a fourchette.

Fluid: As used in this disclosure, a fluid refers to a state of matter wherein the matter is capable of flow and takes the shape of a container it is placed within. The term fluid commonly refers to a liquid or a gas.

Functional Group: As used in this disclosure, a functional group is a specific chemical structure that 1) defines the structure of a chemical family; and, 2) determines the properties of the chemical family. Common functional groups include, but are not limited to, aldehydes, alkanes, alkenes, alkynes, alcohols, amides, amines, carboxylic acids, esters, ethers, haloalkanes, haloalkenes, haloalkynes, and ketones. As a practical matter, the intention of this definition is to use the term functional group in the same manner as the term is commonly used in organic chemistry.

Gas: As used in this disclosure, a gas refers to a state (phase) of matter that is fluid and that fills the volume of the structure that contains it. Stated differently, the volume of a gas always equals the volume of its container.

Glove: As used in this disclosure, a glove is an item of apparel that covers a hand. The glove comprises five finger stalls into which the fingers of the hand are inserted. A glove is further defined with a palm side and a back side. The palm side is proximal to the palm of the hand. The back side is distal from the palm side.

Hand: As used in this disclosure, the hand is the extremity of the arm. The hand attaches to the wrist at the end that is distal from the shoulder. The hand comprises a plurality of metacarpal bones and a plurality of phalange bones.

Hydroxyl: As used in this disclosure, a hydroxyl refers to a functional group comprising the chemical formulation OH. The hydroxyl is the primary functional group that forms alcohols. When unbound, the hydroxyl is considered an ion and is considered to be a radical.

Liquid: As used in this disclosure, a liquid refers to a state (phase) of matter that is fluid and that maintains, for a given pressure, a fixed volume that is independent of the volume of the container.

Loop: As used in this disclosure, a loop is the length of a first linear structure including, but not limited to, shafts, lines, cords, or webbings, that is: 1) folded over and joined at the ends forming an enclosed space; or, 2) curved to form a closed or nearly closed space within the first linear structure. In both cases, the space formed within the first linear structure is such that a second linear structure such as a line, cord or a hook can be inserted through the space formed within the first linear structure. Within this disclosure, the first linear structure is said to be looped around the second linear structure.

Microorganism: As used in this disclosure, a microorganism is an organism too small to be viewed by the unaided eye. Microorganisms are typically single-celled organisms such as bacteria, yeast, viruses, protozoa, fungi, and algae. A pathogen refers to a microorganism that has the potential to cause illness or disease.

N-(4-chlorophenyl)-N'-(3,4-dichlorophenyl)-urea: As used in this disclosure, N-(4-chlorophenyl)-N'-(3,4-dichlorophenyl)-urea (CAS 101-20-2) is an antimicrobial agent commonly found in soaps. N-(4-chlorophenyl)-N'-(3,4-dichlorophenyl)-urea is commonly called triclocarban.

Organic: As used in this disclosure, organic refers to a carbon-based chemical structure. A limited number of (mostly) carbon-based salts are traditionally considered inorganic chemical structures and are excluded from the study of organic chemistry.

Palm: As used in this disclosure, the palm of the hand is identified as the portions of a left hand and a right hand between the fingers and the wrist that contact each other when the left hand presses against the right hand when the left hand and right hand are in alignment. The palm of the left hand is the mirror image of the palm of the right hand.

Patient: As used in this disclosure, a patient is a person who is designated to receive a medical treatment, therapy, or service. The term patient may be extended to an animal when used within the context of the animal receiving veterinary treatment or services.

Phase: As used in this disclosure, phase refers to the state of the form of matter. The common states of matter are solid, liquid, gas, and plasma.

Pre-Moistened Wipe: As used in this disclosure, a pre-moistened wipe is a paper or textile is that previously moistened and that is used for cleaning purposes. By previously moistened is meant that the paper or textile is moistened before the pre-moistened wipe is packaged for storage. These previously moistened papers or textiles will remain moist until subsequent accessed. The previously moistened paper or textile can be individually wrapped for storage or can be stored in bulk. Pre-moistened wipe are commonly referred to as baby wipes or wet wipes.

Relaxed Shape: As used in this disclosure, a structure is considered to be in its relaxed state when no shear, strain, or torsional forces are being applied to the structure.

Sleeve: As used in this disclosure, a sleeve is a tube like covering that is placed over a rod, shaft or other cylindrical object.

Solution: As used in this disclosure, a solution is a uniform mixture of two or more compounds in a liquid phase. The major component selected of the solution selected from the two or more compounds is called the solvent. The components remaining in the two or more compounds are called the solute.

Spring: As used in this disclosure, a spring is a device that is used to store mechanical energy. This mechanical energy will often be stored by: 1) deforming an elastomeric material that is used to make the device; 2) the application of a torque to a semi-rigid structure; or 3) a combination of the previous two items.

Therapeutic: As used in this disclosure, therapeutic is an adjective that refers to a medical, ameliorative, or hygienic substance, process, or procedure. Trank: As used in this disclosure, the trank refers to the portion of a glove that covers the palm and back of the hand.

Water: As used in this disclosure, water (CAS 7732-18-5) is a molecule comprising two hydrogen atoms and one oxygen molecule. The phase of water at normal temperature and pressure is liquid. As used in this disclosure, the definition of water is expanded to include dilute water-based solutions of salts and ionic structures using water as the solvent.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:
1. A sanitary wipe glove comprising
a glove, an elastic band, and a cleansing agent;
wherein the elastic band attaches to the glove;
wherein the cleansing agent is a liquid phase solution that is absorbed into the glove;

wherein the sanitary wipe glove is configured for use with a patient;
wherein the sanitary wipe glove is configured to be worn on a hand of the patient;
wherein the glove is an apparel item;
wherein the glove is worn on the hand of the patient;
wherein the glove is formed from an absorbent material;
wherein the elastic band secures the glove to the hand of the patient during use of the sanitary wipe glove;
wherein the cleansing agent is a chemical solution;
wherein the cleansing agent is an antimicrobial compound that is adapted to be applied to a body of the patient by the glove;
wherein the glove and the cleansing agent are rubbed against the body of the patient;
wherein the glove comprises a trank, a plurality of finger stalls, and an opening;
wherein each of the plurality of finger stalls attaches to the trank of the glove;
wherein the opening is an aperture formed within the trank of the glove;
wherein the trank is a portion of the glove that is configured to enclose a palm of the hand of the patient;
wherein the trank is formed from an absorbent material;
wherein the trank is saturated by the cleansing agent during storage of the glove;
wherein each of the plurality of finger stalls is a tubular structure that is configured to enclose a finger of the hand of the patient;
wherein each of the plurality of finger stalls is sized and positioned to receive a finger from the hand of the patient;
wherein the plurality of finger stalls is formed from an absorbent material;
wherein each of the plurality of finger stalls is saturated by the cleansing agent during storage of the glove;
wherein the trank and the plurality of finger stalls are configured to be rubbed against a body of the patient such that the cleansing agent is applied to the patient during a cleaning process;
wherein a position of the opening in the trank is distal from the plurality of finger stalls;
wherein the opening receives the hand of the patient when the glove is donned;
wherein the elastic band is an elastic loop;
wherein the opening in the trank of the glove is configured to receive the hand of the patient;
wherein the cleansing agent is a liquid phase solution comprising water (CAS 7732-18-5), an alcohol, and an antimicrobial agent;
wherein the water (CAS 7732-18-5) is the solvent used in the solution that forms the cleansing agent;
wherein the alcohol dissolves in the water (CAS 7732-18-5); and
wherein the antimicrobial agent dissolves in the water (CAS 7732-18-5) and alcohol solution.

2. The sanitary wipe glove according to claim 1
wherein the alcohol is an organic chemical compound;
wherein the alcohol is configured to act as a disinfecting agent when applied to a body of the patient; and
wherein the alcohol acts as a preservative that inhibits the growth of bacteria and fungi while the sanitary wipe glove is in storage.

3. The sanitary wipe glove according to claim 2
wherein the antimicrobial agent is an organic chemical compound; and
wherein the antimicrobial agent kills and inhibits the growth of microorganisms found on the skin of the patient.

4. The sanitary wipe glove according to claim 3 wherein the alcohol is 2-proponal (CAS 67-63-0).

5. The sanitary wipe glove according to claim 4
wherein the antimicrobial agent is selected from the group consisting of 5-chloro-2-(2,4-dichlorophenoxy)-phenol (CAS 3380-34-5) and N-(4-chlorophenyl)-N'-(3,4-dichlorophenyl)-urea (CAS 101-20-2);
wherein the 5-chloro-2-(2,4-dichlorophenoxy)-phenol (CAS 3380-34-5) is an antimicrobial and an antifungal compound; and
wherein the N-(4-chlorophenyl)-N'-(3,4-dichlorophenyl)-urea (CAS 101-20-2) is an antimicrobial compound.

6. The sanitary wipe glove according to claim 5 wherein the glove is formed from cotton.

* * * * *